United States Patent
Funk et al.

[11] Patent Number: 5,203,056
[45] Date of Patent: Apr. 20, 1993

[54] HOSE CLAMP FOR MEDICAL APPLICATION

[75] Inventors: Gerald Funk, Bisingen; Tomas Hartig, Hechingen, both of Fed. Rep. of Germany

[73] Assignee: Joka Kathetertechnik GmbH, Hechingen, Fed. Rep. of Germany

[21] Appl. No.: 879,341

[22] Filed: May 7, 1992

[30] Foreign Application Priority Data

Jun. 7, 1991 [DE] Fed. Rep. of Germany ...... 4118732

[51] Int. Cl.$^5$ .................... A44B 21/00; F16L 55/00
[52] U.S. Cl. .................... 24/543; 24/115 G; 251/10
[58] Field of Search .......... 24/543, 115 G, 507, 24/504, 23 W, 499, 481, 487; 251/10

[56] References Cited

U.S. PATENT DOCUMENTS

| | | | |
|---|---|---|---|
| 3,766,925 | 10/1973 | Rubricius | 24/543 |
| 4,053,135 | 10/1977 | Saliaris | 24/543 |
| 4,346,869 | 8/1982 | MacNeill | 251/10 |
| 4,429,852 | 2/1984 | Tersteegen et al. | 24/543 |
| 4,453,295 | 6/1984 | Laszczower | 24/115 G |
| 4,589,626 | 5/1986 | Kurtz et al. | 251/10 |
| 4,673,161 | 6/1987 | Flynn et al. | 251/10 |
| 5,035,399 | 7/1991 | Rantanen-Lee | 251/10 |

FOREIGN PATENT DOCUMENTS 2042131 9/1980 United Kingdom ............. 251/10

OTHER PUBLICATIONS

Thermoplastic Scientifics, Inc. Dura-Clamp For Flexible Tubing, One Sheet, 1979.

Primary Examiner—Victor N. Sakran
Attorney, Agent, or Firm—Michael J. Striker

[57] ABSTRACT

A hose clamp for medical application comprises a bracket-shaped clamping body having bracket ends arrestable with one another to form a closed ring, and provided with openings for a hose which passes through a throughgoing passage extending in a bracket plane. The clamp body has bracket legs. Inwardly directed wedge-shaped clamping jaws are provided on the bracket legs. Side walls are located in both sides of the throughgoing passage parallel to the bracket plane so as to prevent bending out of a hose from the bracket plane.

6 Claims, 1 Drawing Sheet

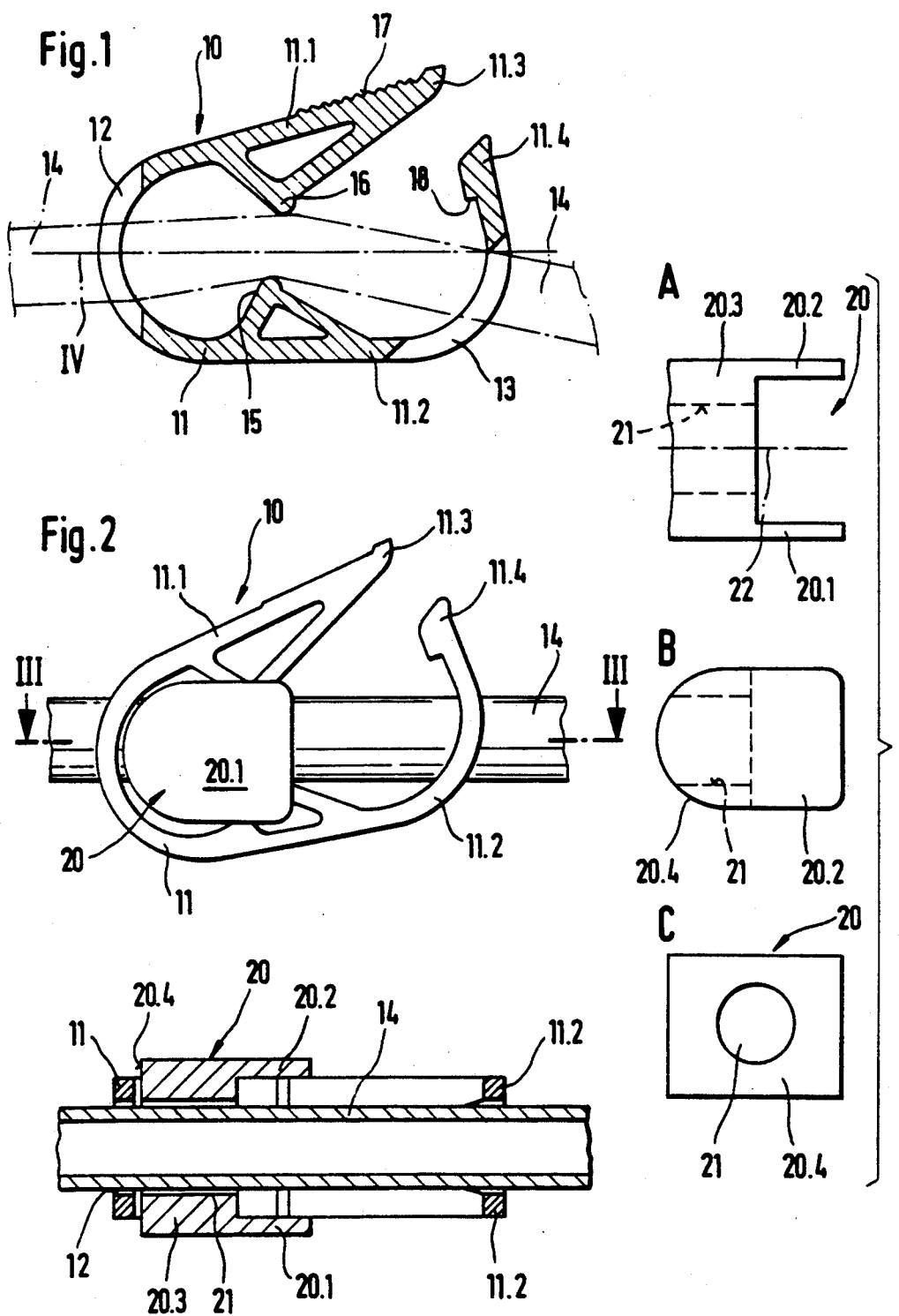

HOSE CLAMP FOR MEDICAL APPLICATION

BACKGROUND OF THE INVENTION

The present application relates to a hose clamp for medical applications.

More particularly, it relates to such a hose clamp which has a bracket-shaped clamp body which is arrestable to form a closed ring and has openings for a throughgoing passage for a hose to be clamped and also inwardly directed wedgeshaped clamping jaws in both bracket legs.

Hose clamps of the above mentioned general type are known in the art. They have a laterally open clamp body so that the hose at the clamping location remains visible from outside. Therefore, there is a danger that a very soft and correspondingly flexible hose can be bent out of the clamp body laterally beyond the bracket plane. As a result, during closing of the hose clamp the clamp jaws no longer engage the hose or engage the latter only partially. This danger is especially substantial when the hose clamp must be placed on curved parts of a hose.

SUMMARY OF THE INVENTION

Accordingly, it is an object of the present invention to provide a hose clamp of the above mentioned general type, which avoids the disadvantages of the prior art.

More particularly, it is an object of the present invention to provide a hose clamp which ensures a reliable engagement of hose by the clamped jaws also in curved regions of a hose.

In keeping with these objects and with others which will become apparent hereinafter, one feature of the present invention resides, briefly stated, in a hose clamp in which at both sides of the throughoing passage, side walls extend parallel to a bracket plane and prevent buckling of a hose arranged in the hose clamp outwardly of the bracket plane.

In accordance with an advantageous feature of the present invention the side walls are dimensioned so that they at least partially laterally cover both clamping jaws.

Due to the side walls, the hose in the immediate vicinity to the clamping jaws is reliably secured from buckling from the plane of the laterally open clamp body. The side walls can be formed directly on the clamp body.

In accordance with an advantageous embodiment, the side walls are formed on a special insert member for the clamp body. This has the advantage that complicated injection molds for a clamping body composed of synthetic plastic material are not needed and the hose clamp can be selectively used with or without the insert member.

For relatively stiff hoses the side walls can be dispensed with as before, and the insert member can be exchangeably arranged in the clamping body.

The insert member which can be simply produced also in injection molds, can be advantageously U-shaped. The legs of the U-shaped insert member can form the side walls and the base of the U-shaped member can be provided with a hose throughgoing opening with an opening axis extending parallel to the side walls.

It is advantageous when the base of the U-shaped insert member is thicker than the side walls, and there the distance between them corresponds at least to the thickness of the clamp body at the location of the insert.

The side walls only insignificantly increase the thickness of the clamp body. They form smooth closing faces which during application of the hose clamp onto the skin of a patient cannot apply unpleasant pressure and abrasion areas on the skin.

The insert member can be clamped by a simple expansion of the bracket legs into the space between both cooperating clamping jaws and the connecting arc of the bracket leg, and unclamped for exchange. When the hose clamp is used, the hose throughgoing opening of the insert member coincides with a throughgoing passage opening for the hose to be clamped, provided in the connecting arc of the clamped body.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 1 is a view showing a central longitudinal section of a clamp body of a hose clamp in accordance with the present invention;

FIG. 2 is a side view of the hose clamp with an insert member clamped in the clam body;

FIG. 3 is a view showing a section through the hose clamp, taken along line III—III in FIG. 2;

FIG. 4 is a view showing the insert member of the hose clamp, on a plan view A, a side view B and an end view C.

DESCRIPTION OF THE PREFERRED EMBODIMENTS

FIG. 1 shows a central longitudinal section of a bracket-shaped clamp body 1 of a hose clamp which is identified as a whole with reference numeral 10 and formed in accordance with the prior art. The clamp body 11 has a first throughgoing opening 12 and a second throughgoing opening 13 for a hose 14 to be clamped, the hose shown with dash-dot line in FIG. 1.

Wedge-shaped clamping jaws 15 and 16 are formed on both bracket legs 11.1 and 11.2 of the clamp body 11. They move relative to one another and clamp the hose 14 when ends 11.3 and 11.4 of both bracket legs 11.1 and 11.2 move relative to one another for closing the bracket-shaped clamping body 11. The end 11.3 of the bracket leg 11.1 is formed as an arresting tongue. An arresting step 18 is formed on the inner side of the end 11.4 of the other bracket leg 11.2. The end 11.3 of the bracket leg 11.1 engage in the arresting step 18 of the bracket end 11.4 of the bracket leg 11.2. The closing of the bracket legs to form a closed ring-shaped clamp body 11 is performed in known manner under the action of a finger pressure applied against an outer corrugated face 17 of the bracket leg 11.1. The opening of the hose clamp is performed under the action of a finger pressure in an outward direction against the end 11.4 of the other bracket leg 11.2.

FIG. 2 shows the hose clamp 10 on a side view with a clipped-in insert member 20. The insert member 20 is shown in FIG. 4 on three views. From FIG. 4 and also from the cross-section shown in FIG. 3, it can be seen that the insert member 20 is U-shaped. The U-shaped insert member 20 has legs which form thin side walls 20.1 and 20.2. The side walls cover the laterally open clamp body 11 from its connecting region provided with a throughgoing opening 12 between both bracket legs 11.1 and 11.2 to both clamping jaws 15 and 16 and also somewhat further outwardly.

The insert member 20 has a base 20.3 which is somewhat thicker than both side walls 20.1 and 20.2. The base 20.3 is provided with a throughgoing opening 21. The longitudinal axis of the opening 21 extends parallel to both side walls 20.1 and 20.2. The insert member 20 has a rounded rear end 20.4 and therefore correspond to the connecting arc of the clamp body 11 in the region of the throughgoing opening 12. The insert member 20 can be clamped between both clamping jaws 15 and 16 in the clamp body 11, by expanding of the bracket legs 11.1 and 11.2.

It will be understood that each of the elements described above, or two or more together, may also find a useful application in other types of constructions differing from the types described above.

While the invention has been illustrated and described as embodied in a hose clamp, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A hose clamp for medical application comprising a bracket-shaped clamp body having bracket ends arrestable with one another to form a closed ring, and provided with openings for a hose which passes through a throughgoing passage extending in a bracket plane, said clamp body having bracket legs; inwardly directed wedge-shaped clamping jaws provided on said bracket legs; and side walls located at both sides of said throughgoing passage parallel to the bracket plane so as to prevent bending out of a hose from the bracket plane; an insert member for said clamp body, said insert member being U-shaped and having legs which form said side walls and a base provided with a hose throughgoing opening which has an opening axis extending parallel to said side walls.

2. A hose clamp as defined in claim 1, wherein said walls at least partially laterally cover said clamping jaws.

3. A hose clamp as defined in claim 1, wherein said insert member is arranged exchangeably in said clamp member.

4. A hose clamp as defined in claim 1, wherein said base is thicker than said legs.

5. A hose clamp as defined in claim 4, wherein said side walls are spaced from one another by a distance which corresponds to at least a thickness of said clamp body in the region of said insert member.

6. A hose clamp as defined in claim 1, wherein said bracket has bracket legs and a connecting arc, said insert member during expanding of said bracket legs of said clamp body being clampable in a space between said clamping jaws and said connecting arc of said bracket legs, where said hose throughgoing opening coincides with a throughgoing opening for a hose to be clamped in said connecting arc of said clamp body.

* * * * *